United States Patent [19]

Liu et al.

[11] Patent Number: 5,163,956
[45] Date of Patent: Nov. 17, 1992

[54] METHODS AND LENTICULES FOR MODIFYING THE CORNEA

[75] Inventors: Yung S. Liu, Niskayuna, N.Y.; Keith P. Thompson, Atlanta; Raymond P. Gailitis, Decatur, both of Ga.; Seth R. Banks, Milwaukee, Wis.; Gary C. Taylor, Fair Oaks, Calif.

[73] Assignee: General Electric Company, Schenectady, N.Y.

[21] Appl. No.: 870,210

[22] Filed: Apr. 13, 1992

Related U.S. Application Data

[63] Continuation of Ser. No. 609,976, Nov. 6, 1990, abandoned.

[51] Int. Cl.⁵ ............................................. A61F 2/14
[52] U.S. Cl. ............................................. 623/4; 623/5
[58] Field of Search ........................ 623/4, 5; 604/22

[56] References Cited

U.S. PATENT DOCUMENTS

| | | | |
|---|---|---|---|
| 4,565,198 | 1/1986 | Koeniger | 128/305 |
| 4,607,617 | 8/1986 | Choyce | 128/1 R |
| 4,646,720 | 3/1987 | Peyman | 128/1 R |
| 4,655,774 | 4/1987 | Choyce | 623/5 |
| 4,662,881 | 5/1987 | Nordan | 623/5 |
| 4,669,466 | 6/1987 | L'Esperance | 128/303.1 |
| 4,676,790 | 6/1987 | Kern | 623/5 |
| 4,693,715 | 9/1987 | Abel, Jr. | 623/5 |
| 4,923,467 | 5/1990 | Thompson | 623/5 |
| 4,941,093 | 7/1990 | Marshall et al. | 364/413.01 |
| 4,969,912 | 11/1990 | Kelman et al. | 623/4 |

*Primary Examiner*—Randy C. Shay
*Attorney, Agent, or Firm*—Marvin Snyder

[57] ABSTRACT

A lenticule is bonded to the eye as part of its formation process by curing or final curing the lenticule on the eye. Such lenticules provide a smooth transition from the body of the lenticule to Bowman's layer on which the lenticule is disposed. The lenticule at the time its material or precursor is placed on the eye may vary from being essentially all viscous collagen which flows and must be molded to obtain a desired lenticule configuration to a substantially stable preform which holds its own shape. Such preformed lenticules may be formed using an appropriate mold and photopolymerization or other partial curing techniques to pre-cure the lenticule material to an appropriate stage for application to the eye.

41 Claims, 10 Drawing Sheets

METHODS AND LENTICULES FOR MODIFYING THE CORNEA

This application is a continuation of application Ser. No. 07/609,976, filed Nov. 6, 1990, now abandoned.

BACKGROUND OF THE INVENTION

1. Field of the Invention

The present invention relates to the field of vision correction and more particularly to methods of modifying the cornea to provide improved vision.

2. Background Information

There is a need for vision correction which does not rely on either glasses or contact lenses. In some cases this need is a result of the fact that glasses and contact lenses are incapable of correcting the vision errors exhibited by a particular eye. In other cases, this results from an occupational or other requirement that the patient have near perfect vision without the use of glasses and contact lenses or because of a desire of the patient to avoid the use of glasses or contact lenses for other reasons. A variety of surgical techniques have been suggested to providing vision correction without the use of contact lenses and glasses. A number of these techniques are described briefly in the background portion of U.S. Pat. No. 4,923,467 entitled "Apparatus and Process for Application and Adjustable Reprofiling of Synthetic Lenticules for Vision Correction" by Keith Thompson; that patent is incorporated herein by reference in its entirety. Another surgical technique, discussed in U.S. Pat. No. 4,923,467, is known as photorefractive keratectomy and involves the use of intense ultraviolet light to remove corneal material by ablation without apparent thermal or mechanical damage to adjacent tissue. This procedure may be carried out using an argon fluoride (ArF) excimer laser at a wavelength of 193 nm. This procedure is irreversible since the removed tissue cannot be replaced. In order to correct vision, this procedure requires removal of corneal material from the central, visually active portion of the cornea and thus carries attendant risks of irreversible damage.

U S. Pat. No. 4,923,467 is directed to a technique for providing a synthetic lenticule which is attached to the cornea as a means to provide vision correction—a procedure which avoids removal of any tissue in the visually active portion of the cornea. In accordance with U.S. Pat. No. 4,923,467 a synthetic lenticule of biocompatible material such as collagen is fabricated to fit the patient's cornea and to provide the refractive changes necessary for vision correction. Such lenticules are attached to the eye by forming a shallow groove in the cornea outside the visually active portion of the cornea, placing an appropriate adhesive in the groove and attaching the synthetic lenticule to the eye by placing the lenticule in the intended position with its periphery disposed in the groove and secured therein by the adhesive. A variety of other techniques may be used for securing the lenticule to the cornea at the groove. This technique has the advantage that since the adhesive is disposed in the groove, the lenticule may be removed if necessary without any affect on the visually active portion of the cornea.

In the event that the lenticule as initially fabricated and attached does not provide the desired degree of correction, or if the eye's characteristics change subsequently so that additional correction is required, the correction provided by the lenticule may be changed by laser ablation of the lenticule itself. This is considered a substantial improvement over the direct ablation of the cornea because the cornea is unaffected by this ablation. Consequently, in the event that the lenticule cannot be corrected by further ablation, the lenticule may be removed and replaced with a substitute lenticule without adverse affect on the central, optically active, portion of the cornea.

A potential disadvantage of this technique is the need to form the peripheral groove for the mounting of the lenticule, the need to accurately configure both the posterior and anterior surfaces of the lenticule to mate with the existing contour of the cornea in order to provide the desired optical correction and to provide a smooth transition between the lenticule and the Bowman's layer of the cornea. Such a smooth transition facilitates the regrowth of epithelial cells across the lenticule in order to re-establish the epithelium as an overlying protective layer which separates the cornea from the exterior environment.

A technique for modifying the configuration of the cornea which retains the advantages of U.S. Pat. No. 4,923,467 while further reducing risks and simplifying procedures is desirable.

OBJECTS OF THE INVENTION

A primary object of the present invention is to provide a means of modifying the configuration of the cornea without invading or penetrating any portion of the cornea except for the temporary removal of the epithelium.

Another object of the present invention is to provide an improved technique for attaching a lenticule to the cornea.

Still another object of the present invention is to form a lenticule on top of the cornea's exterior surface.

A still further object of the present invention is to avoid any exposure of the eye directly to ultraviolet radiation of known mutagenic or inflammatory risk during the application of a lenticule to the eye.

Another object of the invention is to form a lenticule on the cornea without having to accurately configure the posterior surface of the lenticule to mate with the existing contour of the cornea's anterior surface.

Still another object of the present invention is to provide a method of fabrication of the lenticule by directly curing an incompletely cured layer of collagen-containing material which is applied to the exterior surface of the cornea.

SUMMARY OF THE INVENTION

The above objects and others which will become apparent from the specification as a whole, including the drawings, are achieved in accordance with the present invention by placing a precursor of the lenticule on the eye and then curing that precursor to provide a finished lenticule which is bonded to the eye. That precursor may be viscous collagen alone, pre-shaped or partially cured collagen, a preformed lenticule having a posterior surface which is either uncured or only partially cured, at least in the vicinity of the periphery thereof. Where the precursor is viscous collagen, a mold is preferably employed to shape the viscous collagen to the desired configuration of the final lenticule and to retain that shape during curing of the viscous collagen. The use of a mold on the eye is unnecessary with those precursors whose configuration is sufficiently stable during the curing process. The lenticule is preferably directly bonded to the eye during and by the curing process without the use of any grooves or other mechanical connection structures. Where necessary, the lenticule may be reprofiled by laser ablation prior to, during or after the placement to adjust its effect on the cornea's optical power.

A lenticule in accordance with the present invention is preferably applied by preparing the eye for its application, applying a precursor of the lenticule to the eye and curing the precursor to attach the lenticule to the eye. Preparation of the eye preferably includes removal of the epithelium from the region where the lenticule is to be located and attachment of a suction-ring to the eye to hold a mold or lenticule applicator. The precursor is then placed on the eye and appropriately shaped if necessary. Curing is initiated to cure the lenticule and bond it to the eye. The initiation of curing may be prior to or after application of the precursor to the eye, depending on the curing technique being used.

Pre-shaped or preformed lenticules may be preformed and then applied to the eye in accordance with the invention by depositing viscous collagen in the interior of a mold having a configuration to impart the desired anterior configuration to the final lenticule and with a posterior surface suitable for forming the posterior surface of the lenticule to the desired configuration. The lenticule may then be partially pre-cured to a stage at which it may be handled for application to the eye while retaining its desired configuration (surface shape(s)). Where such precuring is photo-induced, the lenticule may be built up in layers if the curing inducing radiation is not sufficiently penetrating to successfully cure a full thickness lenticule. During this prefabrication process, whether done as a single unit or in a layered manner, the central, optically active portion of the anterior surface of the lenticule may be cured more completely than the peripheral and/or posterior portions of the lenticule if desired.

Such a preformed lenticule may be substantially or completely cured and bonded to the eye by providing a bead of viscous collagen along the periphery of the lenticule for bonding the lenticule to the eye and for providing a smooth transition between the lenticule's anterior surface and the anterior surface of the adjacent portion of the eye. Alternatively, additional bonding may be provided by the incompletely cured posterior surface of the lenticule to which appropriate curing mechanisms are applied in situ.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION

Figure 1:
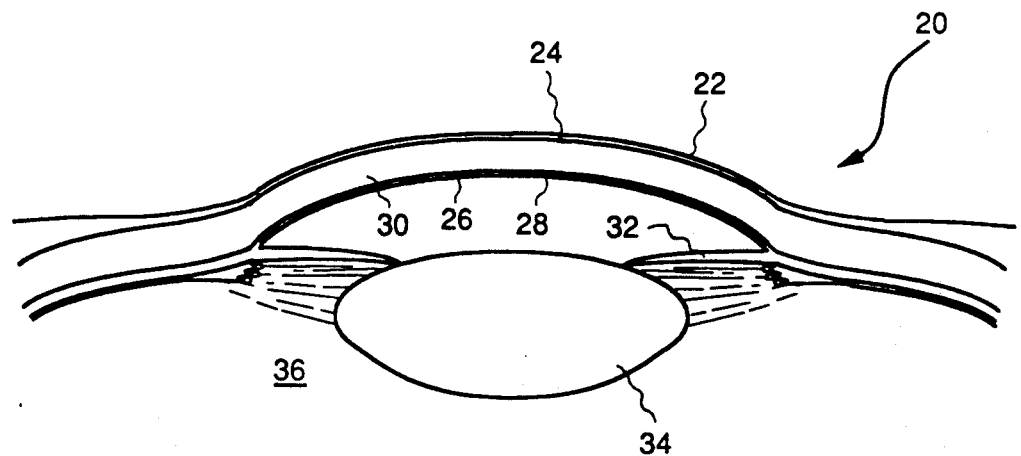
FIG. 1 is a cross-section view of a front portion of the human eye prior to use of the present invention.

In FIG. 1, the front portion of a human eye 18 is illustrated in cross-section. The cornea 20 of the eye comprises five different layers or portions (1) an outer or anterior layer 22 known as the epithelium, (2) Bowman's layer 24 on which the epithelium is disposed, (3) the bulk 30 of the cornea which is known as the stroma, (4) an inner corneal membrane 26 known as Descemet's membrane and (5) an inner or posterior layer 28 known as the endothelium. The iris 32, the crystalline lens 34 and the vitreous region 36 complete the portion of the eye illustrated in FIG. 1. The epithelium is the outer covering or skin of the cornea and is comprised of epithelial cells. The eye in FIG. 1 is illustrated as it appears in its natural, unmodified state.

Figure 2:
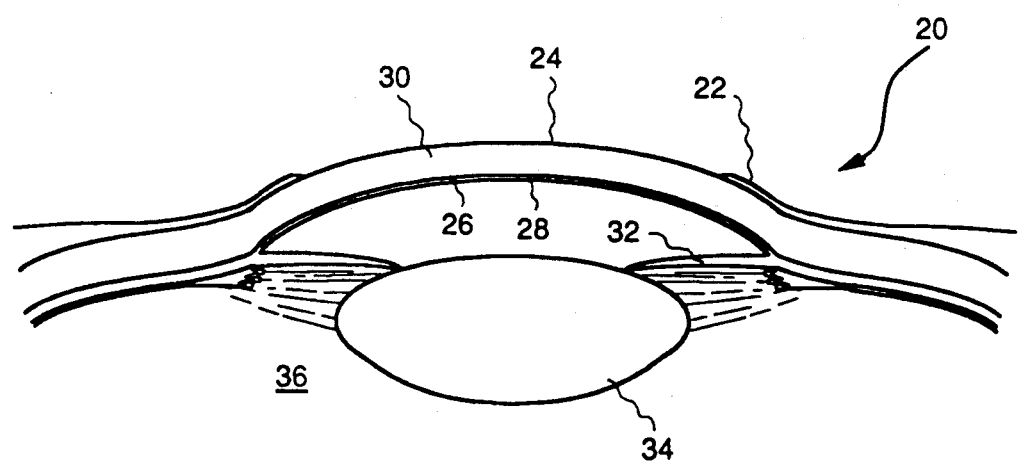
FIG. 2 is a cross-section similar to FIG. 1 showing the eye after removal of the epithelium from the location where a lenticule is to be formed.

If a contact lens were used to correct the vision of this eye, the contact lens would lie on the anterior side of the epithelium 22 with a tear film both between the posterior surface of the contact lens and the epithelium and over the anterior surface of the contact lens. The tear film on the anterior surface of the contact lens is most important to image formation. With the contact lens in that position, it acts effectively as part of the cornea for controlling refraction and thus visual acuity. However, the contact lens is free to shift or rotate relative to the cornea and can cause irritation and infection if not properly cleaned and periodically removed. Where it is desired to permanently modify the shape of the cornea to correct vision problems, a lenticule may be mounted on the cornea in the manner taught in U.S. Pat. No. 4,923,467. The primary difference between a contact lens and a lenticule in this use of the term lenticule is the fact that the lenticule is permanently attached to the cornea and situated between the epithelium layer and Bowman's layer when the attachment is completed. In order to permanently attach such a lenticule, the epithelium 22 must be removed from the portion of the cornea where the lenticule will be attached. Consequently, in preparation for the attachment of a lenticule, the epithelium must be removed to expose the Bowman's layer portion of the cornea as illustrated in cross-section in FIG. 2.

Figure 3:
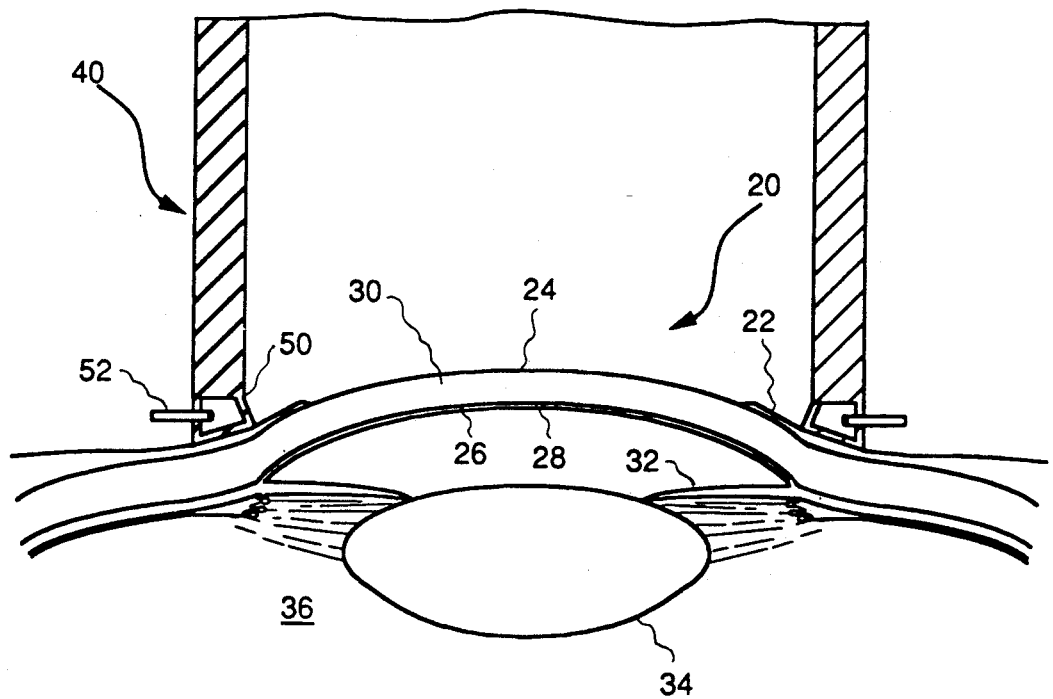
FIG. 3 is a cross-section illustration showing a suction ring mold holder/lenticule precursor applicator attached to the eye.

Once the epithelium has been removed, the eye is ready for the application of a lenticule thereto in accordance with the present invention. In FIG. 3, the eye of FIG. 2 is illustrated again in cross-section with a suction ring fixture 40 attached to the eye. The suction ring fixture 40 is secured to the eye by a suction ring 50 which is open toward the eye and from which air is evacuated via the duct 52 in order to create suction to hold the suction ring fixture fixed to the eye. The suction ring is placed in contact with the cornea around the periphery of the eye in order to avoid distorting the optically active portions of the eye and in order to provide adequate working space within the fixture In FIG. 3, the suction ring fixture is illustrated without attachments. The structure and use of such suction rings is described more fully in U.S. Pat. No. 4,923,467.

Figure 4:
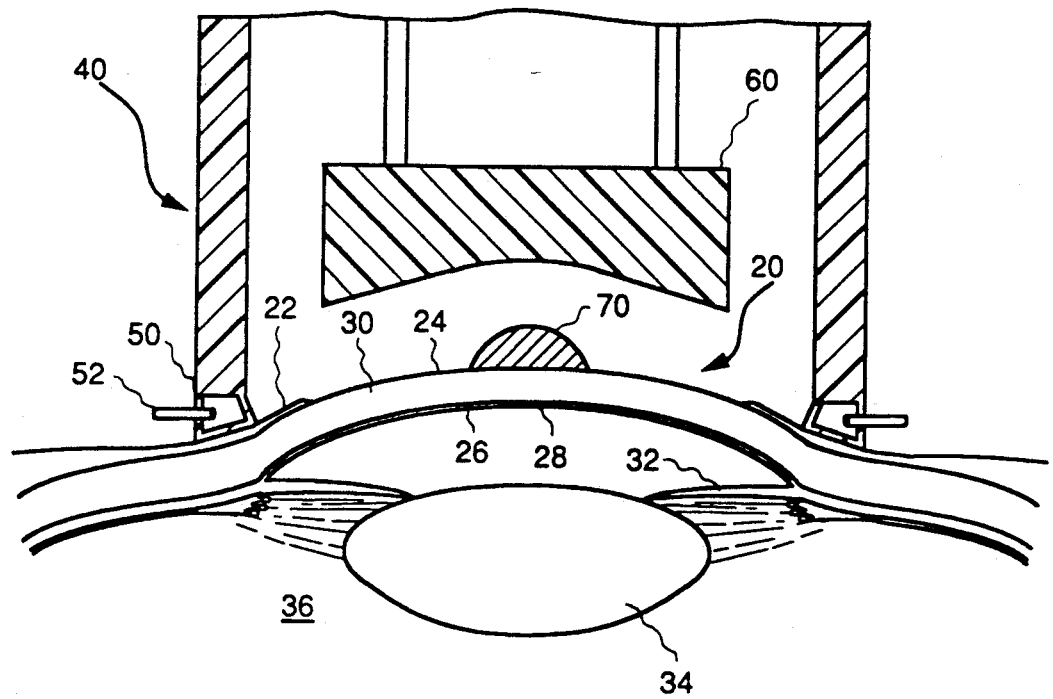
FIG. 4 is a cross-section similar to FIG. 3 showing the eye after the placement of a viscous collagen precursor on the eye.

In FIG. 4, the suction ring fixture 40 is illustrated with a lenticule mold 60 held therein ready for application to the eye. Also illustrated in FIG. 4 is a body 70 of viscous collagen disposed in the central portion of the part of Bowman's layer from which the epithelium has been removed. This viscous collagen is a collagen precursor of the final lenticule. This viscous collagen covers only a portion of the cornea, both in the sense of being smaller in extent than the cornea and in the sense that the epithelium is partially removed prior to placement of the viscous collagen on the eye. The application of this viscous collagen and its shaping into a lenticule are preferably done under reduced pressure or vacuum conditions to minimize gas entrapment within the lenticule and between the lenticule and the portion of the cornea on which the lenticule is disposed. However, it may also be applied at atmospheric pressure since the viscous state of the collagen at the time of its application minimizes gas entrapment between the lenticule and the cornea.

Figure 5:
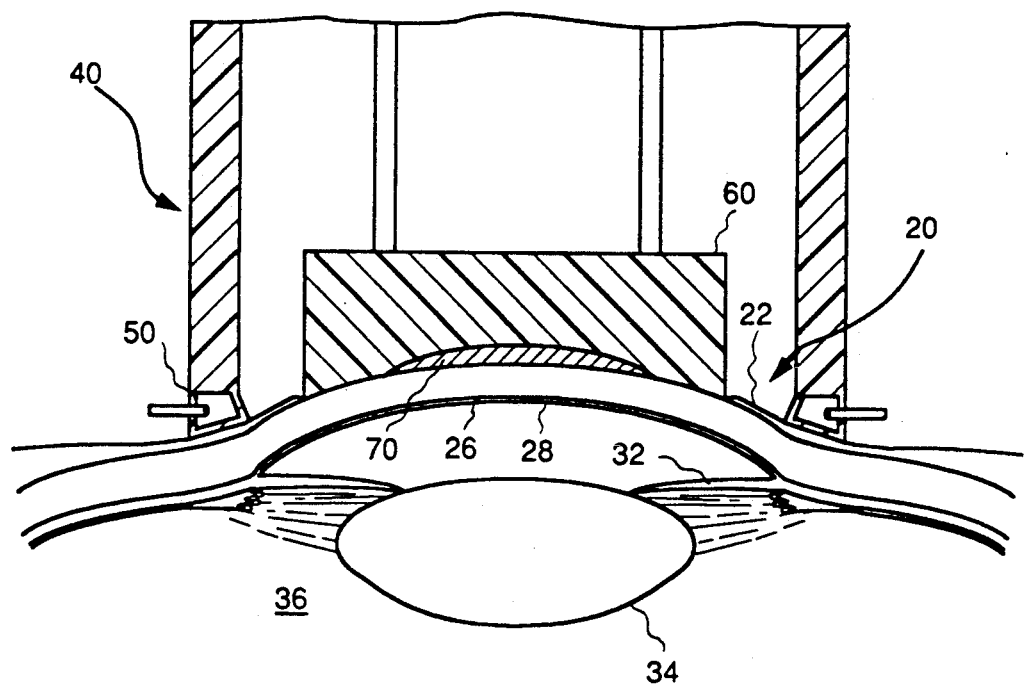
FIG. 5 is a cross-section illustration of a mold held in place during the curing of the viscous collagen of FIG. 4.

In FIG. 5, the mold 60 has been moved into position to shape the viscous collagen 70 into the desired lenticule. This mold is preformed to shape the anterior surface of the lenticule to the configuration desired to correct the vision of that eye. As a result of careful metering and mold design, the quantity of viscous collagen is preferably just sufficient to form the desired lenticule. Viscous collagen typically shrinks during curing. Thus, with such collagens, the mold should be designed to accommodate shrinkage in a manner which ensures that the lenticule has its desired shape when it has finished curing. This may be accomplished by configuring the mold so that the volume of the space between the mold's surface which controls the configuration of the anterior surface of the lenticule and the Bowman's layer can change as the collagen shrinks during curing. This can be done by providing the mold with a resilient or collapsible "gasket" between the body of the mold and Bowman's layer or by forming the mold as two relatively movable pieces, one of which slides relative to the other as the collagen shrinks to maintain the mold cavity's volume the same as the volume of the collagen. A mold with relatively slideable pieces may be configured as a first annular piece having a cylindrical central passageway having the same cross-sectional configuration as is intended for the lenticule and a second, mating plug which fits within that passageway, is slideable toward and away from the eye's surface, which forms a seal with the first annular piece of the mold and has a toward-the-eye surface which is shaped to mold the anterior surface of the lenticule. This ensures that the anterior surface configuration of the finished lenticule will in fact be positively controlled by the mold and that the finished lenticule will be free of voids. Thus, when the lenticule finishes curing, it will have its full desired volume and a smooth anterior surface which will be free of excess blobs, burrs or other protrusions and voids, depressions and other lacks of material.

If desired, the viscous collagen may be placed on the eye in an appropriately small quantity and allowed to slump or flow in accordance with the forces of gravity or other ambient forces whereby the lenticule is formed on the eye without the use of a mold. Such ambient forces may include one or more of cohesive forces, wetting or adhesion effects, capillary forces, the force of gravity, centrifugal force, electric forces (static electricity), magnetic forces as well as others. Such a technique of placing viscous collagen on the eye and curing it without a mold is useful at least (1) where it by nature results in near optimum vision, (2) where the intention is to reprofile the resulting lenticule to provide the desired vision correction, if the naturally occurring lenticule shape does not do so and (3) where a significant function of the lenticule is to smooth an excessively rough anterior corneal surface, which smoothing gives an improved "uncorrected vision" for which more accurate correction can then be determined.

Viscous collagens which are suitable for use in this invention are of the general category known as Type I and our presently preferred material is known as formulation 1F/6.0, available from Autogenesis Technologies, 125 Nagog Park, Acton, Mass. 01720. This collagen material may be cured by exposure to ultraviolet light having wavelengths in the range from 193 nm to 257 nm or longer. However, especially for photopolymerization on the eye, wavelengths near 250 nm are considered undesirable because of their potential mutagenic effects on living cells. Ultraviolet radiation curing of collagens of this general type is a relatively slow process requiring an exposure time of from 10 to 20 minutes.

As an alternative to the use of ultraviolet light as the curing-inducing mechanism, a chemical sensitizer may be included in the collagen mixture which in response to an appropriate frequency and intensity of visible or infrared light initiates curing of the collagen. Such a chemical sensitizer, sometimes referred to as a photo initiator, when triggered by exposure to appropriate stimulation releases radicals which stimulate cross-linking and polymerization and thus the curing of the lenticule. As a further alternative, a curing agent may be mixed with the collagen prior to the application of the collagen to the eye. Such a curing agent may be either active or inactive at the time it is added to the collagen. Such a curing agent is considered inactive if it has no significant curing inducing effect under those conditions. It is considered active if the curing process is initiated at the time of the addition of the curing agent. Different curing agents and different concentrations of them result in different curing times. Either class of curing agent may be employed Curing agents which are inactive at the time they are added to the collagen material are subsequently rendered active at a desired point in time by imposing triggering conditions on that curing agent. Triggering conditions vary with the curing agent and some curing agents have a number of separate triggering conditions any one of which is sufficient to trigger their curing effect. Some curing agents are thermally activated by heating the material to be polymerized. Others are optically triggered by exposure to a wavelength of light which causes the release of the curing promoting species from the curing agent. An appropriate curing promoting compound is formaldehyde or a compound which releases -aldehyde radicals.

As an alternative to photopolymerization induced by ultraviolet, visible or infrared radiation, a chemical curing agent may be mixed with the viscous collagen before the collagen is placed on the eye provided its curing time is long enough to allow proper shaping of the collagen before the collagen becomes too set or cured. One such chemical curing agent is formaldehyde. As a further alternative, a chemical curing agent may be used which is inactive at the time it is added to the collagen. Such an inactive curing agent may later be activated by exposure to light, heat, infrared radiation or other release triggering stimulants which induces release of its curing species. Use of such an initially inactive curing agent allows increased working time prior to curing of the collagen after it is placed on the eye. Where such an initially inactive curing agent is thermally activated, it may be considered desirable to select one which is thermally activated in the vicinity of body temperature whereby the viscous collagen cures naturally as a result of deposition on the eye and more particularly cures from the corneal surface outward rather than throughout its bulk or from its away-from-the-cornea surface inward toward the cornea.

Viscous collagen is sufficiently free of cross linking that it still flows Physically, it is in a non-rigid form which flows in response to the force of gravity. Viscous collagen dehydrates during curing (cross-linking).

Uncured collagen can also be obtained as preformed lenticules. Thus, not all un-cured collagen is viscous collagen. The cured preformed collagen can be distinguished from the uncured preformed collagen by the fact that the uncured preformed collagen will dissolve in an aqueous solution whereas cured preformed collagen will not dissolve Cured collagen does not flow and does not dissolve in aqueous solution. Its physical configuration is stable.

The finished lenticule must be sufficiently cured to be stable in water, tears, and body fluids to which it will be exposed.

As an alternative to placing the viscous collagen on the eye prior to bringing the mold 60 into contact with the eye, the mold 60 may first be brought into contact with the eye and the viscous collagen then gently injected into the resulting cavity to fill that volume.

A variety of techniques may be used to cure this collagen. One technique is to employ an ultraviolet-light-transparent mold and to irradiate the viscous collagen with ultraviolet light having any wavelength in the range from less than 200 nm to less than 250 nm. This ultraviolet light induces polymerization or cross linking of the collagen material. After a sufficient period of exposure which depends on the wavelength and the intensity of the ultraviolet light as well as the characteristics of the collagen itself, the collagen is sufficiently cured to be stable in the environment of the eye. While we prefer to fully cure the collagen, it should be understood that what is needed for the creation of a stable, durable lenticule is that the collagen material be in a form which is stable in the environment of the eye and that the stable condition may be obtained prior to full cross linking or curing of the collagen material. As a consequence, complete curing may not be necessary with particular materials. Thus, we use the term "cured lenticule" to refer to a lenticule which is sufficiently cured to be stable in the environment of the eye.

Figure 6:
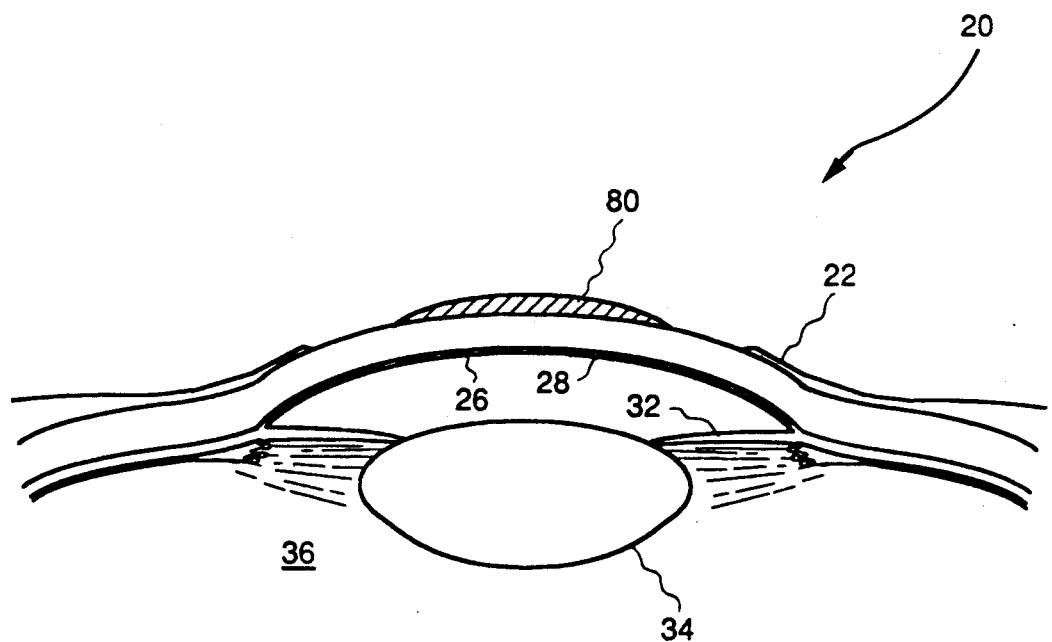
FIG. 6 is a cross-section illustrating the eye after completion of the shaping of the lenticule and its curing.

The eye with the cured lenticule 80 is illustrated in cross-section in FIG. 6. In this figure, it should be noted that the lenticule feathers smoothly into the surface of the Bowman's layer portion of the cornea thereby providing an extremely smooth transition across which the epithelial cells easily grow in order to coat the lenticule with the epithelium. It will be noted that no groove is formed in the cornea at the periphery of the lenticule. This is considered advantageous, because it reduces the invasiveness of the process as compared to the process of U.S. Pat. No. 4,923,467 even though that patent's process is itself minimally invasive since its groove is shallow and well removed from the optically active portion of the cornea.

Figure 7:
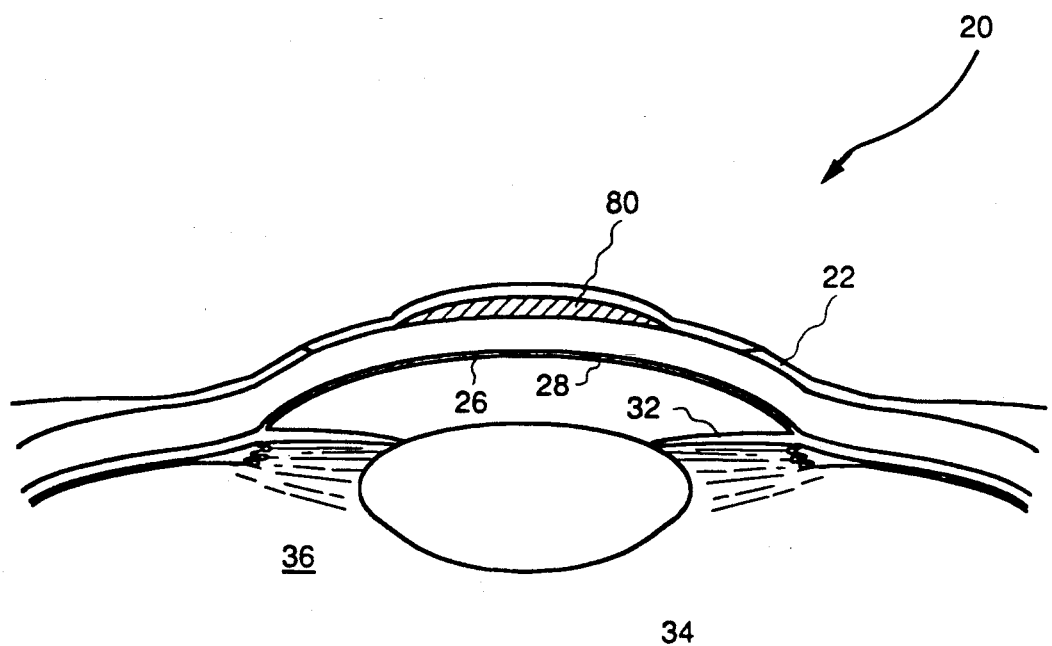
FIG. 7 is a similar cross-section illustrating the eye after growth of the epithelium over the lenticule.

In FIG. 7, the eye 18 is illustrated with the lenticule 80 in place thereon and bonded thereto after the epithelium 22 has grown over the lenticule to return the eye to a condition in which the epithelium is the anterior surface of the cornea across the whole eye. A lenticule of this type is optically and functionally a part of the cornea, since it participates in the refraction of light rays in substantially the same manner as other portions of the cornea and is underneath the epithelium.

A lenticule of this type is substantially permanently bonded to the eye by the curing process. The nature of the resulting bond has not been determined, but it is a sufficiently tenacious bond that it is permanent in the absence of intentional attempts to remove it However, such a lenticule can be peeled off the Bowman's layer by scraping with a blunt scalpel to separate the edge of the lenticule from the cornea and then peeling the remainder of the lenticule off the eye. The adhesion between the lenticule and the Bowman's layer is such that the lenticule appears to come off the Bowman's layer without adverse affect on the Bowman's layer. Thus, the lenticule may be removed if it is determined that a different correction which can not be provided by ablation of the existing lenticule is needed. As an alternative to removing that lenticule, a further collagen layer may be applied thereover to provide a thicker lenticule which will provide the newly required correction.

In order to minimize risk to the central, optically active portion of the cornea in the event that it becomes desirable to remove the lenticule, it may be considered desirable to avoid bonding the central portion of the lenticule to the cornea.

One technique for preventing such bonding is to preform the lenticule prior to applying it to the eye and to fully pre-cure the portion of the lenticule which will be disposed over the central, optically active, portion of the cornea so that during the curing process (which bonds the lenticule to the eye), no bond is created in that central portion of the structure. A lenticule precursor having these characteristics may be fabricated in a number of ways.

Figure 8:
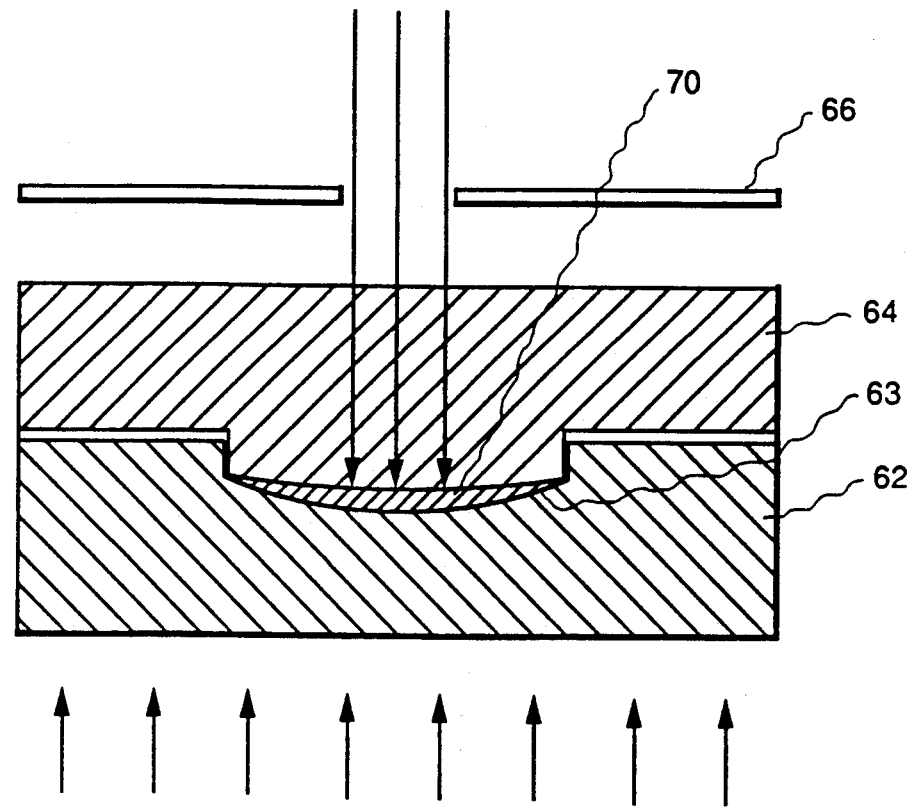
FIG. 8 is an illustration of a method of forming a partially cured, preformed lenticule for use in accordance with the present invention.
Figure 9:
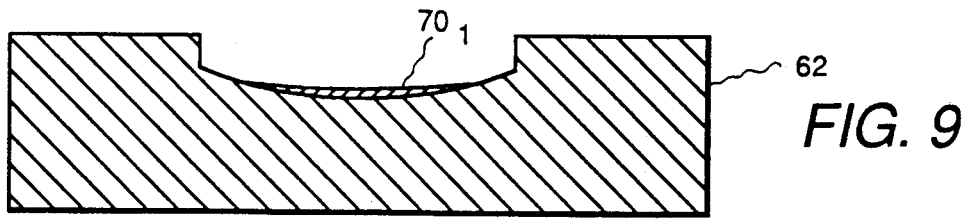
FIGS. 9-12 illustrate steps in a process for forming a preformed lenticule in a multi-step, layered process.
Figure 10:
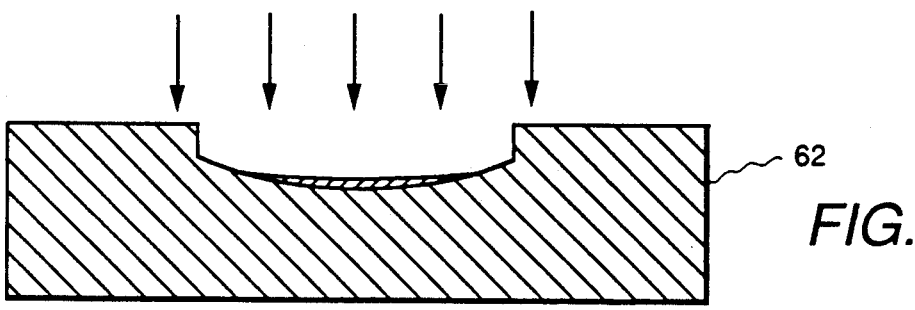

A single step method of fabricating such a preformed lenticule precursor is illustrated in cross-section in FIG. 8 where an anterior mold piece 62 has been shaped to provide a preformed lenticule 74 with a desired anterior contour and a posterior mold piece 64 has been shaped to provide the preformed lenticule with a desired posterior contour which will match the existing contour of the anterior surface of the cornea from which the epithelium has been removed. When the two mold pieces are mated as shown in FIG. 8, the two mold pieces 62 and 64 provide a cavity 63 in which the lenticule is formed with its desire shape and thickness.

The mold is transparent to actinic light which will induce polymerization of the viscous collagen The entire lenticule can be cured to a desired degree by uniform exposure to actinic radiation which will induce polymerization of the collagen. Such uniform actinic radiation is shown impinging on the mold from below in FIG. 8. The extent of such uniform exposure must be controlled to avoid curing any portion of the lenticule to a greater extent than is desired. The central portion of the viscous collagen 70 disposed in the mold may be photo-cured to a greater extent than other portions of that material by exposing that central portion to additional actinic radiation through a mask 66 as shown in FIG. 8 or by using a narrow beam of actinic light whose collimation, beam diameter and beam position restrict it to the central portion of the precursor material disposed in the mold. Depending on the penetration depth in the collagen of this actinic radiation, the lenticule may be cured for its entire depth by light incident on only one side of the mold and viscous collagen, or it may require exposure from both sides to cure the full depth of the viscous collagen. These two different degrees of curing can both be induced by the same frequency and intensity of the actinic radiation with the difference in curing being controlled by the duration of the exposure. Alternatively, different frequencies or intensities of actinic radiation may be used for the different exposures. As an alternative to these multi-exposure techniques, a single exposure may be used with the intensity of the actinic radiation varying with position across the lenticule. Where the degree of curing desired increases as the center of the lenticule is approached from its periphery, a beam having a high intensity near its center and decreasing intensity with increasing distance from its center may be used for such a one step exposure. Once the central portion of the lenticule has been sufficiently cured to prevent bonding and the peripheral portion has been sufficiently cured to enable the lenticule to be handled without damage, the lenticule is placed on the eye and held in its desired position and final curing of the peripheral portion of the lenticule is induced. In this way, the lenticule is bonded to the eye only outside the central, visually active portion of the cornea.

Use of this technique of using a partially precured lenticule precursor has the advantage over the use of an uncured precursor (for which on-the-eye-curing is used for all of the curing of the lenticule's collagen) that exposure of the eye to the actinic radiation is reduced.

In the event that bonding of the lenticule is desired or to be permitted over the entire posterior surface of the preformed lenticule, the front or anterior portion of the lenticule may be fully cured in the central, optically active region in order to fix the configuration of that anterior surface, but without curing that central portion to the full depth of the lenticule. As a result, the entire posterior surface of the lenticule and the peripheral portion of the lenticule may be left incompletely cured and then fully cured in place on the eye.

If a curing agent which is not activated by the light used to pre-cure the lenticule is incorporated in the lenticule, then the final curing of the lenticule may be triggered after the lenticule is in place on the eye without employing optical radiation which could be harmful to the eye. In particular, a thermally activated curing agent may be employed which becomes active at temperatures in the vicinity of normal body temperature, or a visible light photoinitiator may be employed.

Figure 11:
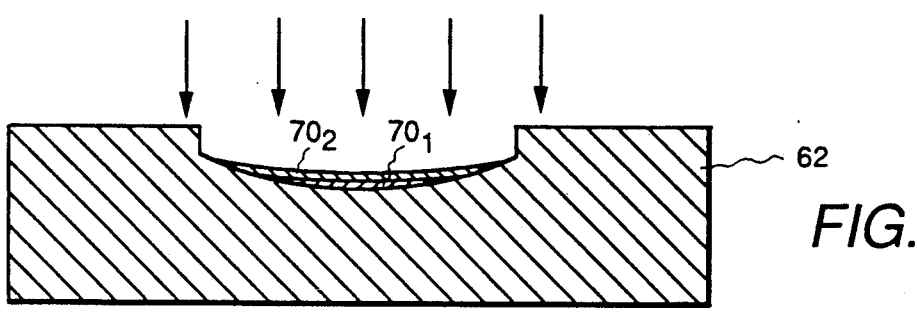
Figure 12:
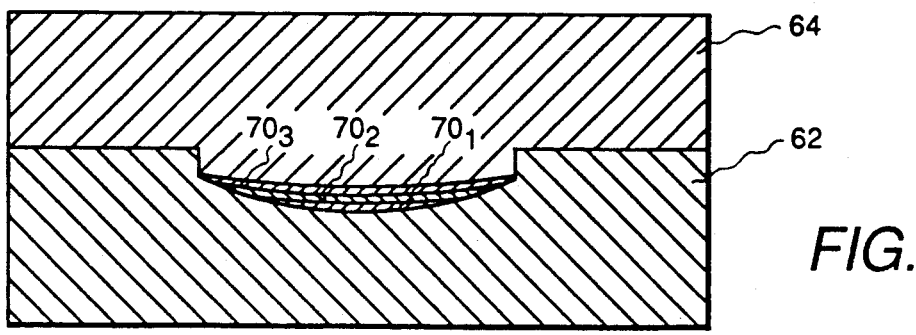

In FIGS. 9-12, a sequence of steps in a layered process of preforming a lenticule similar to that in FIG. 8 is illustrated. This layered process is preferably employed when the radiation it is desired to use to cure or partially cure the collagen does not penetrate the viscous collagen to a sufficient depth to cure the full thickness of a lenticule if it were made in accordance with a single step molding process illustrated in FIG. 8, or may be employed to create layers, i.e., fully-cured anterior layers and partially-cured posterior layers. In this multilayer process, an initial layer $70_1$ of viscous collagen is deposited in the anterior mold 62 in FIG. 9 and is substantially fully cured in the central portion of the lenticule in FIG. 10 by radiation of appropriate frequency and intensity. The entire layer is then cured or partially cured using the same or different radiation as may be appropriate in view of the curing properties of the collagen and the desired condition of the final product. Once this first layer $70_1$ has been cured to the desired extent and in the desired pattern, a second layer $70_2$ of viscous collagen may be disposed over the first layer and cured in a similar manner as shown in FIG. 11. When a sufficient depth has been obtained, the posterior mold segment 64 may be inserted in the mold along with sufficient collagen $70_3$ to fill the remainder of the resulting cavity as shown in FIG. 12. Thereafter, that added collagen $70_3$ may preferably be cured in the same manner as has been discussed for the initial layer or layers unless a different pattern of curing is desired, in which case the pattern of illumination is changed appropriately.

Preformed lenticule precursors of this type may be mounted on and bonded to the eye in a manner which is similar to that which has been described, other than the fact that a mold is not needed where the central portion of the lenticule is sufficiently pre-cured to prevent undesired changes in its shape. However, a similar manipulation apparatus is desirable for accurately positioning the lenticule on the eye.

Figure 14:
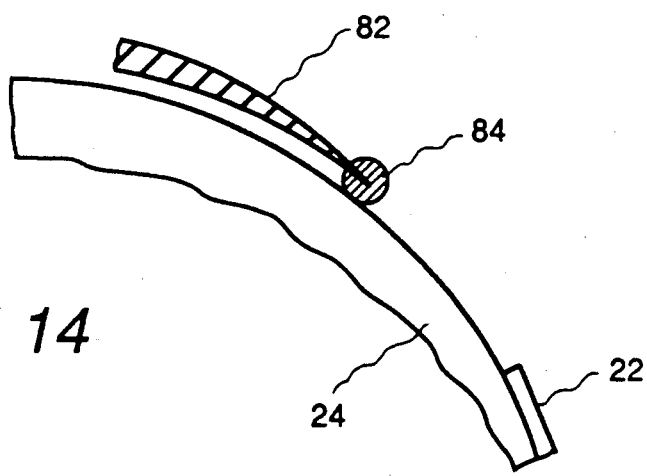
FIG. 14 is a detail in cross-section illustrating the method of bonding this pre-formed lenticule to the eye.

By collagen lenticule precursor, we mean any of (1) viscous collagen, (2) pre-shaped collagen, (3) partially cured collagen, (4) a preformed lenticule which is sufficiently set or partially cured to retain its shape during handling and final curing but which is sufficiently uncured to enable further curing to bond it to the eye, (5) a lenticule in which the anterior surface is fully cured, but the posterior surface is not fully cured with the result that further curing of that collagen in the vicinity of the posterior surface can bond the entire collagen body to the portion of the cornea on which it is placed and (6) a fully cured lenticule in combination with a viscous collagen or preformed collagen bonding bead or region such as illustrated in FIG. 14 (to be discussed hereinafter). Any other appropriate form of collagen may also be used.

A partially cured collagen includes (1) collagen which is uniformly, but incompletely cured, (2) collagen which is non-uniformly cured, either (a) incompletely cured everywhere, but cured to varying degrees or (b) fully cured in some places and uncured or incompletely cured in other places.

By cure or curing of the collagen, we mean crosslinking or otherwise changing the physical or chemical structure of the collagen so that its cured physical condition (shape) becomes stable and the collagen becomes insoluble in body fluids to which it will be exposed and to other fluids to which it may be exposed in the event of the creation of an aperture in the epithelium. So far as we are aware, presently available suitable collagens cure by cross-linking. However, as often happens when a new field becomes a subject of intense research activity, we expect significant technical advances to be made in the development and preparation of suitable materials. In this connection, we recognize that materials which cure or set by mechanisms other than cross-linking may be developed. We consider the use of any such advanced materials in our process to be within the scope of our invention, since (1) their use in our techniques will undoubtedly provide the same benefits or ones similar to those provided by the presently available materials as well as possibly additional benefits and (2) our techniques and processes will provide the same or similar advances and benefits when those advanced materials are used as it does when the presently available materials are used.

Figure 13:
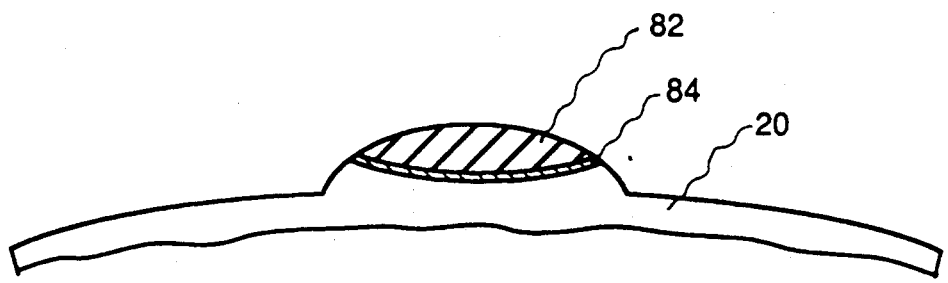
FIG. 13 is a perspective illustration of a preformed lenticule in place on a eye ready for attachment to the eye.
Figure 15:
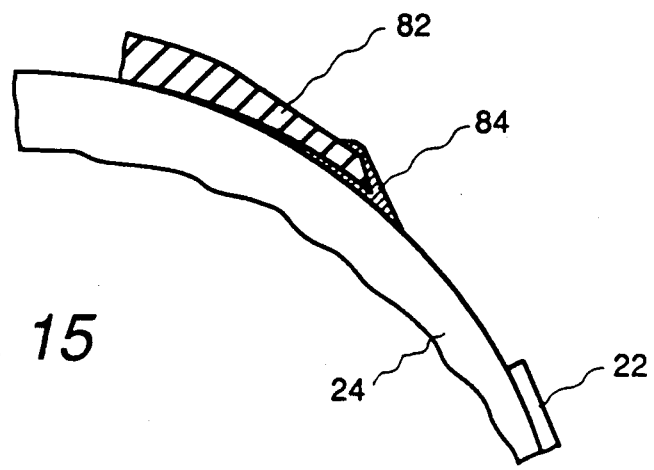
FIG. 15 is a cross-section illustration similar to FIG. 14 illustrating the final configuration of the collagen which bonds the lenticule to the eye.

As an alternative bonding technique, a bead of viscous collagen may be provided adjacent the periphery of the preformed lenticule prior to initiating any on-the-eye curing process. An eye having a lenticule attached by this technique is illustrated in a stylized perspective partially cut away view in FIG. 13 where the dark band indicates the initial location of the bead of viscous collagen and thus, the edge of the lenticule. In FIG. 14 a portion of such a lenticule 82 ready for attachment to an eye is shown in the vicinity of the periphery of the lenticule in cross section. In FIG. 14, the lenticule 82 is fully cured and has a bead 84 of viscous collagen disposed on its peripheral edge. As indicated in FIG. 14, this bead may initially hold the collagen of the cured lenticule above Bowman's layer 24 of the cornea from which the epithelium 22 has been removed. During curing, the viscosity of the viscous collagen becomes less with the result that the collagen flows while in that low viscosity state prior to the viscosity increasing and the collagen setting. In FIG. 15, the lenticule 82 of FIG. 14 is shown in its bonded-to-the-cornea configuration after setting of the collagen 84. It will be noted that the collagen 84 provides a smooth transition from the lenticule 82 to Bowman's layer 24 and provides a bond between the peripheral portion of the lenticule 82 and Bowman's layer 24. Such application of a lenticule should be done under vacuum conditions in order to exclude gas from the region between the lenticule and Bowman's layer to ensure that the lenticule will lie in intimate contact with Bowman's layer following curing of the collagen Once the collagen has cured, atmospheric pressure is slowly reintroduced into the suction ring fixture. Because of the absence of gas between the lenticule and the corneal surface, any potential space between the lenticule and the cornea is eliminated by atmospheric pressure pushing the lenticule against the cornea.

A smooth transition from the lenticule to the uncoated portion of Bowman's layer is considered important for the success of this type of procedure. This process minimizes that problem because the viscous collagen, when in its lowered viscosity state at an early stage in the curing process, has a low enough viscosity that it slumps and flows to form a smooth meniscus which feathers into the Bowman's layer. Such an edge promotes the growth of the epithelium over the lenticule and minimizes any risk of catching the lenticule and partially or completely lifting it off the eye.

Figure 16:
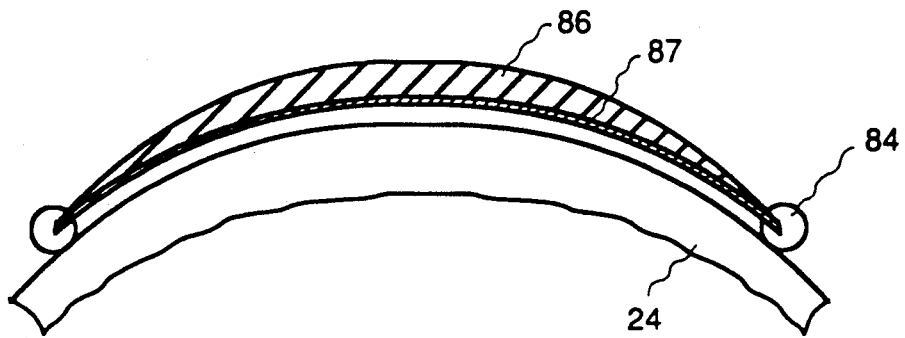
FIG. 16 is a cross-section illustration similar to FIG. 14 illustrating the process of attaching a preformed lenticule which has an incompletely cured posterior surface in combination with the technique of FIGS. 13-15.
Figure 17:
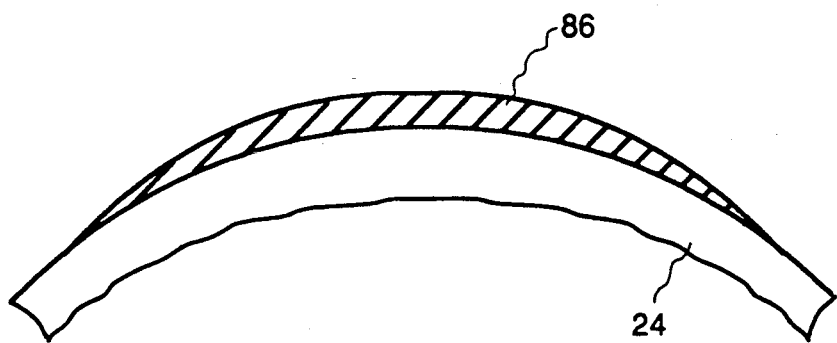
FIG. 17 is a cross-section illustration of the eye and lenticule of FIG. 16 following completion of the curing process.

A further alternative lenticule configuration and bonding technique is illustrated in cross section in FIGS. 16 and 17. The lenticule 86 in FIG. 16 differs from the lenticule 82 in FIG. 14 in that it includes a non-cured or incompletely cured posterior surface portion 87. Following curing, this provides the lenticule-eye configuration illustrated in FIG. 17 in which the entire posterior surface of the lenticule is bonded to the Bowman's layer.

Following completion of the fabrication and attachment of a lenticule in accordance with this invention, the lenticule's configuration may be modified by laser ablation to either increase or decrease its optical power as may be considered desirable after subsequent measurement of the eye's refractive characteristics. This reprofiling may be done in a manner similar to that described in U.S. Pat. No. 4,923,467 or in other background patents and as now well known with respect to the cornea itself in the ophthalmic clinical studies of the use of ablation of the cornea itself for modifying the refractive characteristics of the eye.

While the illustrative embodiments and discussion thereof have been in terms of the lenticule being disposed on the surface of the Bowman's layer portion of the cornea, it should be understood, that the lenticule could be disposed on other portions of the cornea. However, as has been discussed, it is preferred to place it on the undisturbed surface of Bowman's layer in order to minimize the invasiveness of the process.

Normally a lenticule of this type will be generally disk shaped in the sense of being substantially round and free of apertures. However, other shapes and configurations may be used as may be desired, including those with one or more apertures therein and those having other common geometric shapes and those having irregular shapes such as triangular, rectangular, star shaped or any other shapes, including letters and numerals. These other shapes can include ones which are selected entirely for their external appearance. Such lenticules can also incorporate dyes with the collagen in order to make the lenticule externally visible and cosmetic in appearance.

While the invention has been described in detail herein in accord with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A method of correcting vision comprising:
preparing an eye for application of a lenticule thereto by removing the epithelium from a portion of the cornea to expose the Bowman's layer of the cornea;
placing a quantity of uncured collagen as a lenticule precurser on said eye; and
inducing said collagen to cure into a shape which will improve vision and to adhere to said eye as said lenticule.

2. The method recited in claim 1 wherein the step of preparing said eye comprises:
fixing the position of said eye relative to apparatus for placing, said collagen.

3. The method recited in claim 2 wherein said step of fixing the position of said eye includes the step of:
attaching a suction ring to said eye.

4. The method recited in claim 1 further comprising, after the step of placing, the step of:
shaping said collagen on said eye prior to completion of the curing of said collagen.

5. The method recited in claim 4 wherein the step of shaping is performed prior to substantial curing of said collagen.

6. The method recited in claim 4 wherein the step of shaping comprises:
positioning a mold in a desired position relative to said eye, said mold being configured to constrain the surface of said collagen in contact therewith to have a substantially predetermined contour.

7. The method recited in claim 6 wherein:
said positioning step is performed after said placing step.

8. The method recited in claim 6 wherein:
said mold is kept in place over said collagen until said collagen is at least partially set.

9. The method recited in claim 4 wherein the step of shaping said collagen comprises:
allowing the shape of said collagen to be controlled by ambient forces.

10. The method recited in claim 1 further comprising:
positioning a mold in a desired position relative to said eye before said placing step, said mold being configured to constrain the surface of collagen in contact therewith to have a substantially predetermined contour.

11. The method recited in claim 1 wherein the step of inducing comprises:
exposing said collagen to radiation which induces cross-linking of said collagen to form said lenticule.

12. The method recited in claim 11 wherein:
said radiation is ultraviolet radiation.

13. The method recited in claim 11 wherein:
said radiation is visible light; and
said collagen includes a sensitizer which, in response to visible light, releases chemical species which induce cross-linking of said collagen.

14. The method recited in claim 1 further comprising:
adding a curing agent to said collagen, said curing agent being one which induces cross-linking of said collagen to form said lenticule.

15. The method recited in claim 14 wherein:
the step of adding is performed prior to the step of placing.

16. The method recited in claim 15 wherein:
said curing agent is substantially evenly distributed throughout said collagen prior to said placing step.

17. The method recited in claim 14 wherein:
the step of adding is performed after the step of placing.

18. The method recited in claim 14 wherein said curing agent is inactive when it is added to said collagen and said method further comprises the step of:
exposing said collagen to trigger conditions which trigger said curing agent to become active to induce said cross-linking to cure said collagen.

19. The method recited in claim 18 wherein:
said collagen is exposed to said trigger conditions prior to being placed on said eye.

20. The method recited in claim 18 wherein:
said collagen is exposed to said trigger conditions after being placed on said eye.

21. The method recited in claim 1 wherein:
said step of placing uncured collagen comprises placing viscous collagen.

22. The method recited in claim 21 wherein the step of inducing comprises:
exposing said collagen to radiation which induces cross-linking of said collagen to form said lenticule.

23. The method recited in claim 21 further comprising:
adding a curing agent to said collagen prior to the step of placing, said curing agent being one which induces cross-linking of said collagen to form said lenticule.

24. The method recited in claim 23 wherein:
said curing agent is substantially evenly distributed throughout said collagen prior to said placing step.

25. The method recited in claim 1 further comprising the step of:
contouring the anterior surface of said lenticule to provide a desired optical effect.

26. The method recited in claim 25 wherein:
said contouring is performed after curing of the collagen which forms said lenticule.

27. The method recited in claim 1 wherein the step of preparing said eye comprises:
fixing the position of said eye relative to apparatus for shaping said collagen.

28. The method recited in claim 1 wherein the step of preparing said eye comprises:
fixing the position of said eye relative to apparatus for treating said collagen.

29. A method of providing an eye with an artificial member comprising:
preparing said eye for receipt of said artificial member by removing the epithelium from a portion of the cornea to expose the Bowman's layer of the cornea;
placing an uncured collagen as a precurser of said artificial member on said eye; and
curing said collagen to render it stable and to bond to said eye as said artificial member.

30. The method recited in claim 29 wherein:
said step of placing uncured collagen comprises placing viscous collagen.

31. The method recited in claim 30 wherein:
said step of placing uncured collagen further comprises placing pre-shaped, shape-retaining collagen.

32. The method recited in claim 31 wherein:
said pre-shaped collagen is partially cured prior to the step of placing and said inducing step comprises inducing further curing of said precursor 33. The method recited in claim 29 wherein
said step of placing uncured collagen comprises placing pre-shaped, shape-retaining collagen.

34. The method recited in claim 33 wherein:
said step of placing pre-shaped collagen comprises placing collagen that is partially cured.

35. The method recited in claim 29 wherein:
the step of placing comprises placing said collagen on a portion of the cornea; and
after curing, said artificial member is a functional portion of said cornea.

36. The method recited in claim 29 further comprising forming said collagen precursor by:
pre-shaping a viscous collagen; and
partially curing said pre-shaped viscous collagen to render it handleable.

37. A method of providing an eye with a modified cornea comprising:

preparing said eye for modification of said cornea by removing the epithelium from a portion of the cornea to expose the Bowman's layer of the cornea;

placing a collagen precurser of a modification to said cornea on a portion of said cornea; and inducing said precurser to cure and to adhere to said cornea to provide said cornea with a modified configuration.

38. The method recited in claim 37 comprising, performing the following step prior to the step of placing:

partially curing said collagen precursor.

39. The method recited in claim 38 wherein the step of partially curing said collagen precursor comprises:

curing said collagen precursor to an extent which renders said collagen precursor sufficiently stable to enable said collagen precursor to be handled without losing its shape.

40. A method of providing a smooth surface for an initially rough-surfaced cornea comprising:

preparing said cornea to receive a collagen precurser of a lenticule by removing the epithelium from a portion of the cornea to expose the Bowman's layer of the cornea;

depositing viscous collagen on said cornea; and curing said collagen while allowing the shape of said collagen to be controlled by ambient forces.

41. A method of attaching a collagen lenticule precurser to an eye comprising:

preparing said eye by removing the epithelium from a portion of the cornea to expose the Bowman's layer of the cornea;

providing a bead of viscous collagen along the periphery of a preformed lenticule;

positioning said lenticule in a desired location on said eye; and curing said viscous collagen and any incompletely cured collagen at the posterior surface of said lenticule to bond said lenticule to said eye and to provide a smooth transition between the lenticule and the Bowman's layer of said eye.

* * * * *